Figure 1:
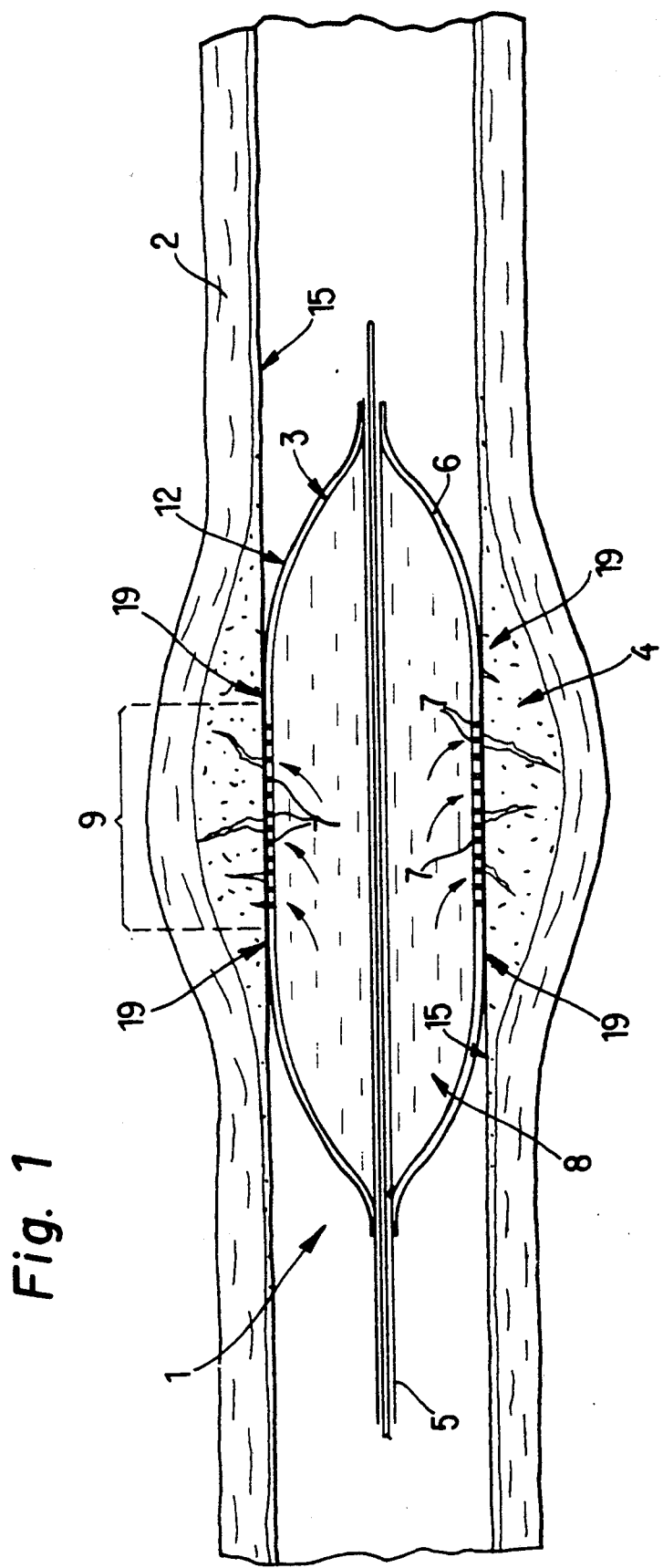

United States Patent [19]
Just et al.

[11] Patent Number: 5,232,444
[45] Date of Patent: Aug. 3, 1993

[54] DILATATION CATHETER

[76] Inventors: Hansjörg Just, Kreuzkopfsteige 11; Ulrich Solzbach, Spechtweg 15, both of D-7800 Freiburg, Fed. Rep. of Germany

[21] Appl. No.: 635,625
[22] PCT Filed: Jun. 21, 1989
[86] PCT No.: PCT/DE89/00408
  § 371 Date: Feb. 25, 1991
  § 102(e) Date: Feb. 25, 1991
[87] PCT Pub. No.: WO89/12478
  PCT Pub. Date: Dec. 28, 1989

[30] Foreign Application Priority Data
  Jun. 25, 1988 [DE] Fed. Rep. of Germany ....... 3821544

[51] Int. Cl.⁵ ............................................. A61M 29/00
[52] U.S. Cl. .......................................... 604/96; 604/53
[58] Field of Search ........................... 604/93, 96-103, 604/264, 265, 280, 51-54

[56] References Cited
U.S. PATENT DOCUMENTS
3,981,299 9/1976 Murray .............................. 604/96 X
4,417,576 11/1983 Baron .............................. 604/96 X FOREIGN PATENT DOCUMENTS
2311807 9/1973 Fed. Rep. of Germany.
3235974 6/1983 Fed. Rep. of Germany.
3516830 11/1986 Fed. Rep. of Germany.

*Primary Examiner*—John D. Yasko
*Attorney, Agent, or Firm*—Peter K. Kontler

[57] ABSTRACT

A catheter for dispensing medication into a body passage or cavity has a hollow shaft and an elongated, inflatable and deflatable member at one end of the shaft. The shaft functions to permit inflation and deflation of the elongated member. The elongated member, which serves as a carrier for the medication, has an intermediate portion centrally located between the ends of the elongated member and a lateral portion on either side of the intermediate portion. Each of the lateral portions extends from the intermediate portion to a respective end of the elongated member. The intermediate portion is perforate to permit the medication to be forced out of the elongated member and into a body passage or cavity when the elongated member is subjected to pressure during inflation. The lateral portions are imperforate so that they can serve as seals upon coming into contact with body tissue as the elongated member is inflated.

33 Claims, 4 Drawing Sheets

DILATATION CATHETER

BACKGROUND OF THE INVENTION

The invention relates to a catheter having a ballon.

In the medical field, especially in radiology and cardiology, the expansion (dilatation) of constrictions (stenoses) along the arteries is currently a frequently used and highly satisfactory method of increasing the blood flow, and thus the supply of oxygen and energy, to the peripheral vascular system.

Here, a so-called dilatation catheter is pushed to the appropriate, stenosed blood vessel segment where the balloon at the leading end is expanded.

A frequent complication of the expansion of blood vessel constrictions is the formation of thrombi in the blood vessels. This often has severe consequences for the patient, especially in the region of the heart, and the difficulties will be described below with particular reference to the coronary situation.

To mitigate the above complication, various medications including, among others, dissolving agents which are to redissolve the thrombi, are dispensed via an intracoronary route (proximal and distal to the balloon) during, before and after the expansion. However, at the time of the actual expansion and the intracoronary thrombus formation induced by the same under certain circumstances, the expanded balloon prevents these medications from penetrating to the desired location. The medications can actually arrive at the dilatation area only after the balloon has been contracted or withdrawn from the expanded region of the stenosis. Under certain circumstances, however, this can be too late for effective action.

Thrombi which have formed in the area of dissections, for example, can readily cause an embolism in the peripheral system or be the starting point for a spontaneous thrombotic blockage. Also, lesions can increase the susceptibility of the inner blood vessel layer to coagulum formation.

The German Offenlegungsschrift 32 35 974 discloses a catheter which can deliver medications to the region of a stenosis during the dwell time of the catheter. Here, expandable balloons are disposed on either side of a stenosis and bound the area of the stenosis from the front and the back. A medication is then delivered to the region between the balloons via openings in the catheter wall. A disadvantage is that the medication can act only while the catheter is in the blood vessel which requires long dwell times with associated drawbacks. Penetration of the medication into the wall itself is very unsatisfactory because, as a rule, the blood vessel wall is undamaged. Hence, active metabolic and diffusion processes, which require relatively long times, have been contemplated. This is disadvantageous particularly since a catheter can quasi-block the blood vessel for only a relatively short period, e.g., seconds to at most a few minutes. However, it is questionable whether the catheter of the German Offenlegungsschrift 32 35 974 can provide an effective treatment within this short interval.

U.S. Pat. No. 4,423,725 also shows an arrangement having a plurality of balloons. Two of the balloons can be expanded on either side of a location to be treated and then seal the zone between the balloons. In addition, a third balloon is provided intermediate the sealing balloons and contains a medicinal active substance which can be dispensed in the zone between the sealing balloons.

To this end, flow apertures are distributed over the surface of the middle balloon, and the active substance can exit through the flow apertures to arrive, for the most part, in the intermediate zone between the two outer balloons. Here, also, penetration of the medication directly into the blood vessel wall during delivery of the active substance is inadequate and an extended dwell time of the catheter is therefore required to achieve penetration by diffusion and the like. Moreover, the structure of this balloon catheter, which contains three individual balloons, is complicated.

Finally, an implantable medication carrier, which is designed to deliver an active substance over an extended period of time, is known from U.S. Pat. No. 3,279,996. This medication carrier includes a capsular body having a porous outer wall through which the active substance can slowly diffuse. Delivery of the active substance within a short time span is neither contemplated nor possible here.

It is an object of the invention to create a catheter of the type indicated at the outset which makes it possible to medicinally treat the dilated blood vessel region which the balloon is expanded. The required dwell time of the catheter for effective treatment is to be substantially reduced. Moreover, the range of applications of the catheter is to be increased and it is to be usable for the treatment of hollow organs also.

To achieve this object, it is proposed that the longitudinal ends of the balloon be provided with sealing zones next to a central region and at the outer side of the balloon which is intended to contact the hollow organ, and that the pores or the like be arranged in the central region with spacing from the ends of the balloon.

A balloon catheter in which the balloon wall is provided with openings in the region of heating zones is already known from the German patent 35 16 830. However, these openings serve for irrigation of the balloon and are to prevent tissue from sticking to the balloon. Furthermore, blood is to be completely expelled from the area between the balloon wall and the blood vessel wall by means of the openings.

This catheter is neither intended nor suited for targeted infiltration or "pressing" of a medicinal active substance into a predetermined treatment zone. Per the intended use, the openings in the balloon wall are specifically arranged to irrigate the intermediate region between balloon and tissue However, this is possible only during a thermal treatment where contact with the tissue just exists but not where an appropriate pressure is applied during expansion of the stenosis.

In contrast, the invention makes it possible for specific wall segments of a blood vessel or hollow organ to be enriched with an active substance. This enrichment already takes place upon dilatation by infiltration of the wall under pressure. During dilatation, smaller and larger pores, tears, lesions and even dissections open up or are forcefully formed in the inner wall of the blood vessel since part of the lumen is expanded by a multiple upon dilatation and the inner wall of the blood vessel can only withstand this process to a limited extent. Immediately following dilatation, such artificially created openings in the wall—due to mechanical-elastic restoring forces—can partially reclose.

In this manner, the action of highly effective medications can be developed at a precise time, and thus optimally, so that side effects during the expansion of blood vessel constrictions and the like can be markedly reduced. The disposition of the pores in the central region and at a distance from the ends of the balloon creates sealing zones adjacent the stenosis to the front and back of the latter. The sealing zones can largely prevent the active substance leaving the central region of the balloon from flowing off to the sides in an undesired fashion. This also prevents a pressure drop which would affect penetration of the active substance into the tissue to the degree contemplated here.

Due to mechanical expansion of the stenosis to the point where dissections form, the tissue opens so that the active substance can be forced in within a short period. In a manner somewhat comparable to an injection, a depot for the active substance is created in the tissue and makes it possible to achieve an active period essentially equal to the dwell time of the catheter. This, in turn, provides the substantial advantage, especially in the coronary region, that occlusion of the blood vessel during dilatation can be eliminated within a very short period.

Active substances are here understood to mean primarily those medications which are capable of dissolving fresh thrombi with varying degrees of efficiency (so-called thrombolytics or dissolving agents) and/or are capable of preventing a new blockage for moderate and long periods of time.

The active substance can further be a substance selected from the group of fibrin adhesives which "cement" tears in the intima or media of the artery by means of local coagulation processes. This avoids the possible consequences associated with the formation of a false lumen and the formation of a thrombus by contact between the deeper exposed wall structures and the blood. Moreover, the use of many medications (nitro, $Ca^{++}$-*antagonists*, etc.) which are effective in blood vessels is contemplated. Good medicinal treatment of hollow organs such as, for example, bladder, gall bladder, stomach, intestine, ureter, bronchi and the like, is likewise possible with the balloon catheter of the invention. Here, also, the active substance can be applied directly to the location to be treated.

In an embodiment where the wall of the balloon is provided with a plurality of pore-like through apertures and the active substance to be applied is disposed inside the balloon, the dilating medium expediently contains the medication or the like to be applied or itself constitutes this medication.

The active substance can therefore travel through the wall of the balloon during dilatation directly to the inner wall of the blood vessel or hollow organ.

According to another embodiment, one or more compartments for the active substance can be provided internally in the region of the balloon wall. The compartments have pore-like apertures opening to the outside and are sealed on the inside.

Upon dilatation, the active substance in the compartments is delivered to the exterior due to the pressure increase within the balloon and thus arrives at the inner wall of the blood vessel or hollow organ in the desired fashion.

A further embodiment of the invention has a plurality of compartments which are sealed from one another with neighboring compartments accommodating different active components.

On the one hand, this allows a plurality of different active substances to be stored and then dispensed during expansion. When using adhesive, it also becomes possible to employ multicomponent adhesives. Here, the different components are stored in alternating individual compartments and are only combined and activated upon issuing during dilatation.

In another embodiment, the outer side of the balloon carries a porous, sponge-like layer which is located between the sealing zones, contains an active substance and can be at least partially compressed when urged against the wall of the blood vessel or hollow organ. The active substance is then liberated from the outer layer upon pressing of the latter against the inner wall of the blood vessel or hollow organ and, in particular, is thus liberated in the region of the greatest counterpressure.

A urine catheter having a sponge-like, expandable zone is known from the German Offenlegungsschrift 23 11 087. However, this sponge-like zone functions to fix the catheter when the sponge-like zone is contacted by liquid and also functions to create a blockage capable of inhibiting infections which occur. This catheter is not suited for the introduction of medications into the blood vessel wall or for the deposition of medications, which are subsequently forced into the blood vessel wall by expansion, in the sponge.

According to yet a further embodiment of the invention, the exterior of the balloon is provided with a separable annular layer which preferably can bind to the inner wall of the blood vessel or hollow organ and contains the active substance. Upon dilatation, the annular layer is pressed against the inner wall of the blood vessel or hollow organ and, under appropriate circumstances, adheres thereto. When the balloon is collapsed, the outer skin of the balloon and the annular layer are separated so that the balloon can be withdrawn. The annular layer remains in the treatment zone and can release its active substance there.

In an expedient additional embodiment, the annular layer and the like consists of resorbable material. This has the advantage that no foreign bodies remain, e.g., in the coronary system, for an extended eriod and that the tunnel-like structure implanted in the artery or the like is destroyed after some time and is then no longer present. In this manner, foreign body complications are avoided.

Figure 2:
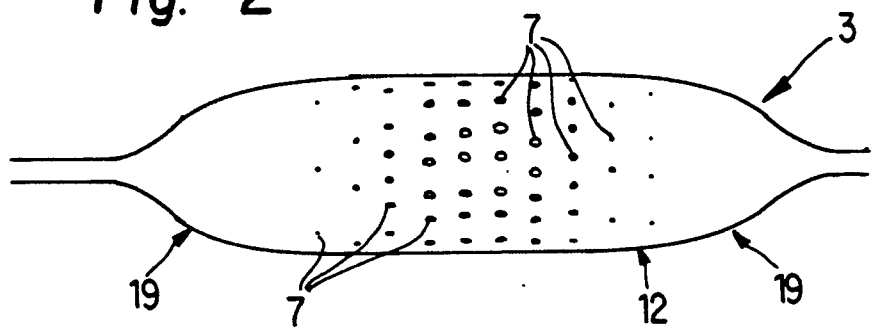
Figure 3:
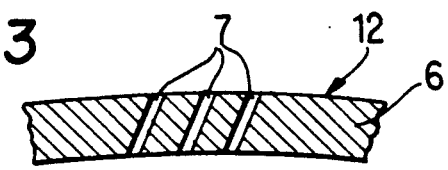
Figure 4:
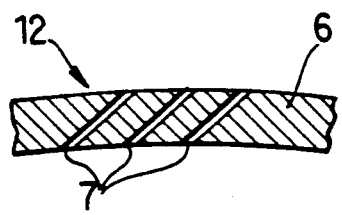
Figure 5:
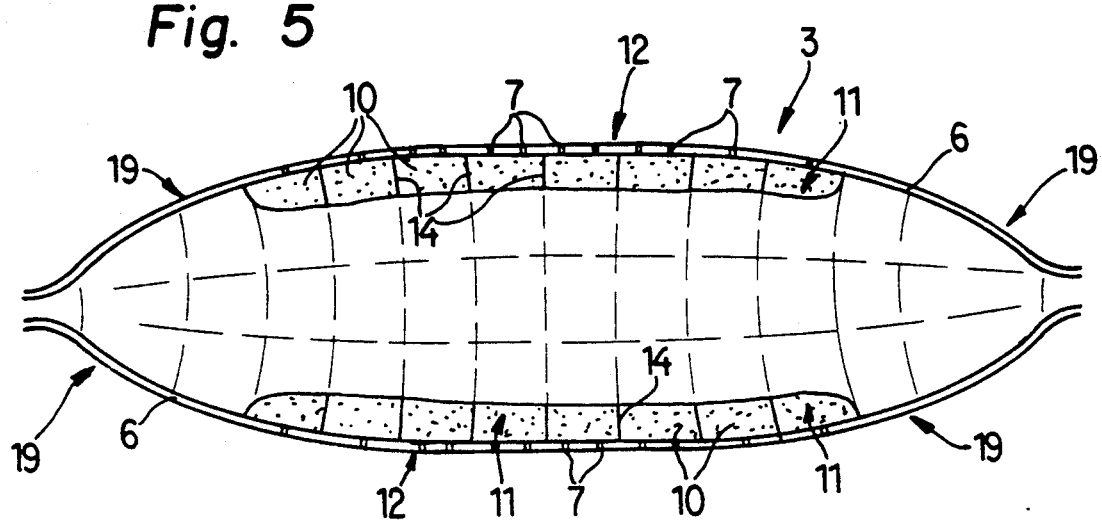
Figure 6:
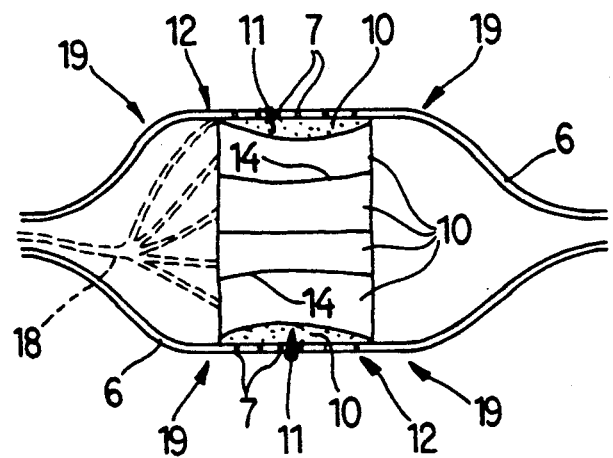
Figure 7:
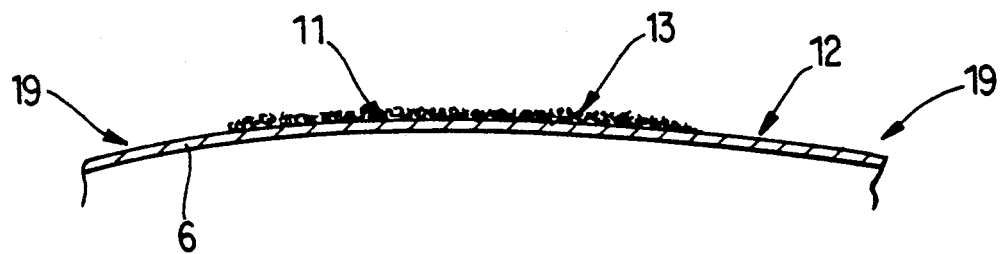
Figure 8:
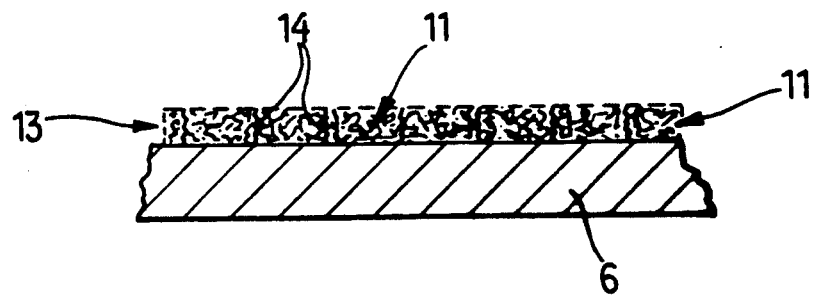
Figure 9:
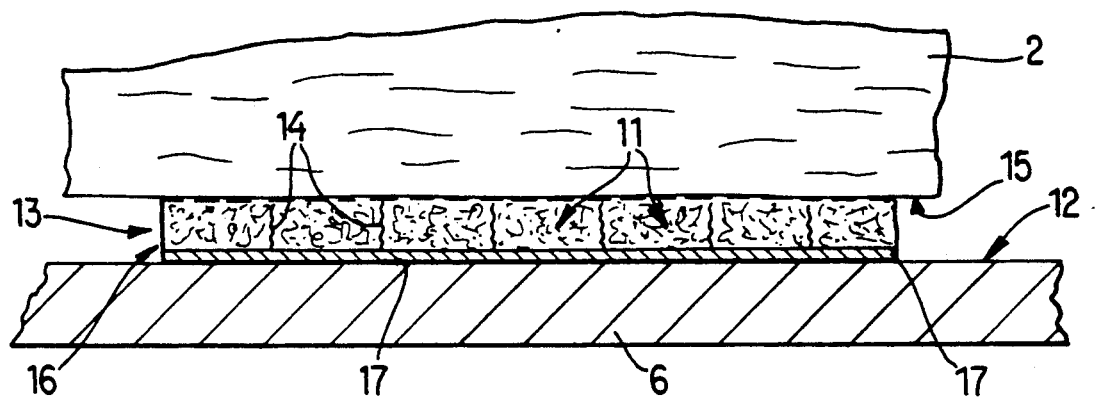
Figure 10:
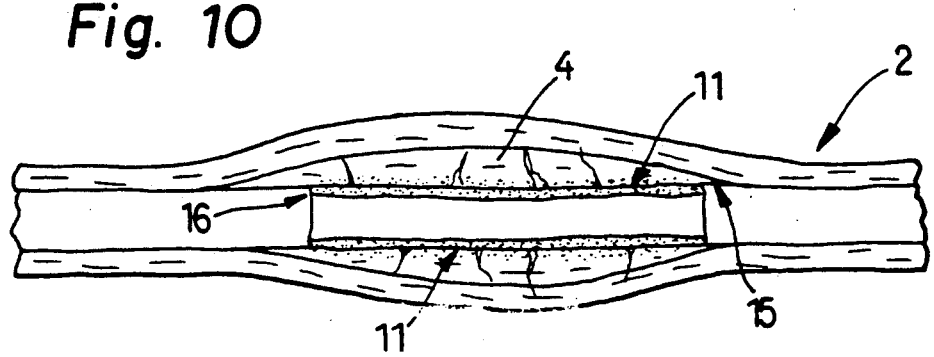

Further embodiments of the invention are recited in the subclaims. The invention and its important details are more fully described below with reference to the drawings. There is shown:

FIG. 1 a fragmentary longitudinal sectional view of a blood vessel and a balloon catheter inside the same, FIG. 2 a schematic exterior view of a balloon constituting part of a balloon catheter, FIGS. 3 and 4 fragmentary sectional views of an outer wall of a balloon in collapsed condition and expanded condition of the balloon, FIG. 5 a schematic side view of a balloon with interior compartments for an active substance, FIG. 6 a schematic view of a modified embodiment of a balloon having internal compartments, FIG. 7 a fragmentary view of a balloon wall having an external, sponge-like layer, FIG. 8 an enlarged detail view of FIG. 7, FIG. 9 a fragmentary longitudinal sectional view of an expanded balloon and an external, separable annular layer, and FIG. 10 a fragmentary view of a blood vessel with a dilated stenosis and an annular layer therein.

In FIG. 1, a dilatation catheter 1 is situated i a blood vessel 2 and, at its inner catheter end, has a balloon 3 which has been expanded in the region of a stenosis 4. The balloon 3 is expanded by means of a dilatation medium (gas or liquid) which can be supplied via the catheter shaft 5.

According to the invention, the balloon 3 is a carrier for an active substance to be applied to the region of a stenosis, for example. For the present invention, the term active substance includes, in particular, medications, thrombolytes and adhesive.

In the embodiment of FIG. 1, the wall 6 of the balloon 3 has a plurality of pore-like through apertures 7 so that, upon dilatation, an active substance in the balloon can exit and become operative in the region of the stenosis. The dilatation medium 8 in this embodiment contains the medication to be applied or constitutes this medication. The apertures 7 are dimensioned such that the dilatation medium 8 containing the active substance can issue only upon expansion of the balloon. As a rule, therefore, this occurs only after a specific internal pressure, which develops during the actual expansion of the stenosis, is reached. The active substance arrives directly at the inner wall of the blood vessel in the region of the stenosis so that any dissections which may occur there undergo direct medicinal treatment. In particular, this can substantially reduce a "prolapse" of stenosis parts in the interior of the blood vessel, with an accompanying formation of a false lumen and also a thrombus, since the medication can act sufficiently by the time the balloon is withdrawn to prevent these complications. Due to infiltration of the wall, the action of the applied medication or the like also extends to the deeper wall or tissue layers. The medication or active substance should exit exclusively or predominantly in the region of the contact area between the balloon 3 and the stenosis 4. Accordingly, in the embodiment of FIG. 1 and also FIG. 2, the pore-like apertures 7 are located in the central region 9 of the balloon as considered longitudinally and are spaced from its ends. It is possible for the apertures 7 to be distributed approximately uniformly over the annular central region of the balloon (FIG. 1). Alternatively, as shown in FIG. 2, the number and/or cross sections of the apertures can decrease from the central region to the outside. The total cross section of the apertures in the balloon wall 6 thus decreases from the central region of the balloon, as considered longitudinally, to the ends thereof.

Adjacent to the central region 9 are sealing zones 19 which prevent the medication introduced through the apertures 17 from flowing off to the sides. This can be readily seen in FIG. 1. The single balloon 3 thus has three regions, namely, two outer sealing zones 19 and a central delivery region 9 for medications or the like.

FIGS. 3 and 4 show a balloon wall 6 having pore-like apertures 17 which are inclined to the surace of the balloon wall. FIG. 3 illustrates the balloon wall in collapsed condition of the balloon and FIG. 4 illustrates the same wall section in expanded condition of the balloon. It is clearly seen that stretching of the balloon wall 6 here leads to a reduction in the cross sections of the apertures 7 thereby preventing a nonuniform increase in the outflow of medication with increasing pressure. A sort of "saturation" is accordingly achieved and causes the outflow of the active substance to be relatively independent of the internal pressure increase of the balloon. In this connection, it is also to be mentioned that this effect is desired primarily while the balloon is being expanded and its outer side does nót yet contact the stenosis 4 over a larger area. The subsequent contact of the balloon wall with the inner side of the stenosis or the inner side of the blood vessel of itself already prevents an increased outflow of medication.

However, to facilitate passage of the medication when the balloon contacts the region of the stenosis, the apertures 7 can be so arranged or designed that compression, and thus an increase in the cross sections of the apertures 7, takes place as the balloon wall meets increased resistance due to contact with the stenosis.

It is still to be mentioned that the total cross section of the apertures in the balloon wall is related to the external and internal pressures acting on the balloon in such a manner that, independent of the internal pressure, a well-defined outflow of the active substance, at a constant rate above a predetermined pressure if necessary, is obtained during dilatation. Since the apertures 7 are fine, pore-like openings, it is assured that a requisite counterpressure for dilatation can be generated inside the balloon.

FIGS. 5 and 6 show a modified embodiment of the invention where a plurality of compartments 10 for the active substance are provided within the balloon 3. The active substance 11 is indicated by dots in FIGS. 5 to 10.

The compartments 10 are sealed relative to one another and to the inside whereas the balloon wall 6 has pore-like apertures 7 in the region of these compartments. In the embodiments of FIGS. 5 and 6, it can likewise be seen that, similarly to the embodiment of FIGS. 1 and 2, the compartments 10 are provided in the central region only. The sealing zones 19 are again disposed on either side thereof.

The embodiments of FIGS. 5 and 6 provide a separation between the dilatation medium and the active substance which may be desirable in some applications. The increased internal pressure of the balloon 3 upon dilatation causes the active substance 11 to be delivered to the outside via the pore-like apertures 7 in the wall 6. Instead of a plurality of compartments which are sealed with respect to one another, a single, e.g., continuous, annular chamber, which is sealed on the inside relative to the interior of the balloon and communicates with the exterior via apertures 7, can be provided if necessary.

The design with one or more compartments 10 also has the advantage of improved control over the amount of medication which can flow out. Moreover, less medication, some of which is very expensive, is required.

In a construction with a plurality of compartments, different active substances, or different components of an active substance, can be accommodated in the individual compartments. For instance, it is then possible to store a multicomponent adhesive whose components issue only upon dilatation to thereupon mix with each other and become activated. When using an adhesive, a balloon material which is inert with respect to this adhesive is selected to prevent adhesion of the balloon in the region of the stenosis.

FIGS. 7 and 8 illustrate another possible embodiment of the invention where the outer side 12 of the balloon carries a porous, sponge-like layer 13 containing an active substance. This layer 13 is constructed in such a manner that it is at least partially compressed upon being urged against the blood vessel wall and thereby releases the active substance contained therein to the outside. The sponge-like layer 13, also, can be divided into individual compartments by dividing walls 14 so that it can accommodate different medications or different components.

In the embodiment of the invention illustrated in FIGS. 9 and 10, the outer side of the balloon 3 is provided with a separable annular layer 16 which can bind to the inner wall 15 of the blood vessel and conains the active substance 11.

The balloon is expanded to such an extent in FIG. 9 that the annular layer 16 which, on its outer side, is provided with the porous, sponge-like layer 13 containing the active substance 11 contacts the inner wall 15 of the blood vessel. By further increasing the pressure in the interior chamber of the balloon 3, the layer 13 is then increasingly compressed so that the active substance accommodated therein flows out. In the embodiment with a separable annular layer 16, at least portions of the layer 13 contain an adhesive which creates a sufficiently strong connection between the inner wall of the blood vessel and the annular layer 16. The strength of this connection is selected to be greater than that of the connection between the annular layer 16 and the wall 6 of the balloon. Consequently, the annular layer 16 is separated from the outer side 12 of the balloon as soon as the balloon is collapsed which can be accomplished by generating a suitable vacuum in the interior of the balloon.

After separation, the balloon can be withdrawn and the annular layer 16 then remains in the region of the stenosis. In this manner, active substances can be dispensed in the neighboring blood vessel segments for an extended period of time. Furthermore, this also results in mechanical stabilization of the region of the stenosis A tunnel-like annular layer 16 in the region of the stenosis is shown in FIG. 10 where the dilatation catheter has already been removed.

As indicated in FIG. 9, the outer side of the balloon can be provided with a parting layer 17 which confronts the separable annular layer 16, is inert to adhesive and prevents the annular layer 16 from sticking to the balloon 3 after the cementing procedure.

The entire annular layer 16 including the sponge-like outer layer 13 and the like preferably consists of a material (e.g., cellulose) which is resorbable by the body so that no foreign bodies remain in the coronary system for extended periods. With this design, the tunnel-like structure originally implanted in the artery and constituting a separating layer disappears after some time. This allows complications which can occur with implanted parts to be avoided.

FIGS. 1 to 10 show individual means for applying an active substance to the region of a stenosis. If necessary, these individual means can be combined. For example, the balloon can be provided with a porous, sponge-like layer 13 containing an active substance and with one or more compartments 10 which are preferably disposed adjacent to the sponge-like layer. It is also possible, in combination with the sponge-like layer 13 and, if necesssary, in addition to the compartments also, to provide perforated wall segments through which the active substance can exit from the interior of the balloon.

Overall, the design of the dilatation catheter 1 of the invention makes it possible, during the dilatation procedure, to dispense medications directly to the critical locations in the region of the stenosis where thrombi and/or dissections form. The balloon can here be kept in expanded condition and "retain the shape" of the stenosis until the medications have acted to such an extent that the balloon can be made smaller and withdrawn largely without danger. Complications which would otherwise arise can be largely eliminated in this manner.

FIG. 6 indicates in broken lines that the compartments 10 are connected with a conduit 18 (if necessary, with a plurality) which leads to the outside and can be used to refill the compartments 10 with an active substance. The conduit 18 is suitably guided inside the shaft of the catheter.

In addition to using the catheter of the invention for the expansion of constrictions in the coronary region as illustrated in the Figures, the catheter can be employed for treatments inside hollow organs. For instance, it is possible to carry out a cytostatic delivery directly to and into the wall of a changeable, tumorous hollow organ such as a bile duct, intestine, ureter, etc. Furthermore, active substances having an anti-inflammatory effect, for example, can be applied to mucous membranes, bronchi, nasal mucous membranes, etc. whereas cauterizing and astringent active substances can be applied to locations where an enlargement of the lumen is desirable (strictures or constrictions in the region of the air passages or in the gastrointestinal tract).

Particularly when the catheter 1 of the invention is used in the region of the air passages, the treated location actually blocked by the balloon can be kept (air-) permeable via a bypass which traverses the balloon 3 in the longitudinal direction.

All of the features set forth in the description, claims and drawings can be material to the invention either alone or in any combination.

We claim:

1. A catheter for treating a body passage or cavity, particularly for treating stenoses in blood vessels, comprising an inflatable and deflatable member having a pair of spaced lateral portions which include opposed ends of said member, and an intermediate portion between said lateral portions, said member further having an external peripheral surface which includes a sealing section at each of said lateral portions and a perforate section at said intermediate portion provided with a plurality of openings, said sealing sections being arranged to bear against body tissue when said member is inflated in the body, and said member being devoid of openings between said intermediate portion and said ends; and means for inflating and deflating said member.

2. The catheter of claim 1, wherein said member is elongated and said ends are longitudinal ends of said member.

3. The catheter of claim 1, wherein said intermediate portion is substantially centrally located between said ends.

4. The catheter of claim 1, wherein said member comprises means for accommodating a treating substance to be dispensed into a body passage or cavity.

5. The catheter of claim 4, further comprising a treating substance in said accommodating means.

6. The catheter of claim 1, wherein said openings have an approximately uniform distribution over said intermediate portion.

7. The catheter of claim 6, wherein said intermediate portion is substantially annular.

8. The catheter of claim 1, wherein said member comprises a balloon and said openings are provided in said balloon.

9. The catheter of claim 8, wherein said openings are arranged so that the cross-sectional areas of said openings decrease in response to inflation of said balloon.

10. The catheter of claim 1, wherein each of said openings constitutes part of a flow passage which is inclined to said perforate section of said peripheral surface.

11. The catheter of claim 10, wherein each of said flow passages deviates from a straight line.

12. The catheter of claim 11, wherein said flow passages zigzag.

13. The catheter of claim 1, wherein said openings are arranged so that the cross-sectional areas of said openings increase in response to exertion of pressure on said perforate section of said peripheral surface.

14. The catheter of claim 1, wherein said member has an axis passing through said ends and the total cross-sectional areas of said openings, as considered in planes substantially normal to said axis, decreases from the center of said member towards said ends.

15. The catheter of claim 1, wherein at least one of the number of said openings per unit area and opening cross-sectional area decreases from the center of said member towards said ends.

16. The catheter of claim 1, further comprising a fluid for inflating said member, said fluid containing or constituting a treating substance to be dispensed into a body passage or cavity.

17. The catheter of claim 1, wherein said member has a hollow interior which accommodates at least one compartment for a treating substance to be dispensed into a body passage or cavity, said one compartment being sealed from said interior and communicating with at least one of said openings.

18. The catheter of claim 17, further comprising a conduit which connects said one compartment with the exterior of said member.

19. The catheter of claim 18, wherein said inflating and deflating means comprises a hollow shaft and said conduit is disposed in said shaft.

20. The catheter of claim 17, wherein said one compartment is located adjacent to said perforate section of said peripheral surface.

21. The catheter of claim 1, wherein said member is provided with a plurality of compartments which are sealed from one another, each of said compartments communicating with at least one of said openings and accommodating at least part of a treating substance to be dispensed into a body passage or cavity.

22. The catheter of claim 21, wherein two neighboring compartments accommodate different components of a multicomponent treating substance.

23. The catheter of claim 1, wherein said intermediate portion comprises a compressible, sponge-like external layer containing a treating substance to be dispensed into a body passage or cavity.

24. The catheter of claim 1, wherein said member comprises an external layer which is separable from said member and contains a treating substance to be dispensed into a body passage or cavity.

25. The catheter of claim 24, wherein said layer is substantially annular.

26. The catheter of claim 24, wherein said layer is capable of binding to body tissue.

27. The catheter of claim 24, wherein said layer comprises a resorbable material.

28. The catheter of claim 24, wherein said layer comprises at least one of a sponge-like material and a compartment for accommodating said treating substance.

29. The catheter of claim 28, wherein said layer has an inner side and said inner side is impermeable to said treating substance.

30. The catheter of claim 24, wherein said layer has an inner side and said member comprises a parting layer in contact with said inner side.

31. The catheter of claim 30, wherein said parting layer is substantially inert to adhesive.

32. The catheter of claim 1, wherein said member comprises a sponge-like layer containing a treating substance for a body passage or cavity and at least one compartment to accommodate a treating substance for a body passage or cavity.

33. The catheter of claim 1, wherein said member comprises a balloon and a sponge-like layer on said balloon containing a treating substance for a body passage or cavity, said balloon being provided with at least one of a perforate portion and a compartment to accommodate a treating substance for a body passage or cavity.

* * * * *